United States Patent [19]

Lin

[11] Patent Number: 4,687,747

[45] Date of Patent: Aug. 18, 1987

[54] PHENANTHRIDINIUM ESTER AS A LABELLING COMPOUND IN LUMINOMETRIC IMMUNOASSAY

[75] Inventor: Wayne H. T. Lin, Chesterfield, Mo.

[73] Assignee: Mallinckrodt, Inc., St. Louis, Mo.

[21] Appl. No.: 626,781

[22] Filed: Jul. 2, 1984

[51] Int. Cl.[4] ................. G01N 33/543; C07D 221/12
[52] U.S. Cl. ................... 436/518; 436/527; 436/531; 436/800; 436/805; 436/810; 435/8; 546/108
[58] Field of Search ............. 546/108; 435/8; 436/527, 531, 800, 805, 810, 518

[56] References Cited

U.S. PATENT DOCUMENTS 4,193,983  3/1980  Ullman ................. 436/528

FOREIGN PATENT DOCUMENTS 1461877   1/1977  United Kingdom .
4445778  11/1978  United Kingdom .
8133207  11/1981  United Kingdom .
8137522  12/1981  United Kingdom .

OTHER PUBLICATIONS

Weeks Clinical Chemistry 29(8) pp. 1474–1479, (1983).
Woodhead et al., *Luminescent Assays: Perspectives in Endocrinology and Clinical Chemistry*, pp. 147–155, 1982.
Patel et al., *Luminescent Assays: Perspectives in Endocrinology and Clinical Chemistry*, pp. 181–189, 1982.
Kemp et al., *Proc. Natl. Acad. Sci. USA*, vol. 78, No. 7, pp. 4520–4524, 1981.
Weeks et al., *Clinical Chemistry*, vol. 29, No. 8, pp. 1474–1479, 1983.
Wannlund et al., *Luminescent Assays: Perspectives in Endocrinology and Clinical Chemistry*, pp. 125–128, 1982.
Erhlich, H. et al., *Methods Enzymol*, 68, pp. 443–453, (1979).

*Primary Examiner*—Robert J. Warden
*Assistant Examiner*—Robert Benson
*Attorney, Agent, or Firm*—Bernard, Rothwell & Brown

[57] ABSTRACT

Disclosed are novel chemiluminescent compounds and their method of use in luminometric immunoassays. The compounds, comprising salts of phenanthridinium esters, are particularly useful in sandwich immunoassays.

15 Claims, 2 Drawing Figures

RABBIT IgG LIA STANDARD CURVE

PHENANTHRIDINIUM ESTER AS A LABELLING COMPOUND IN LUMINOMETRIC IMMUNOASSAY

FIELD OF THE INVENTION

This invention lies in the art of immunoassay procedures and is particularly concerned with compounds which enable detection of immunological substances or other analytes through chemiluminescence.

BACKGROUND OF THE INVENTION

Immunoassay is an analytical technique widely used in medicine and the biological sciences. The term "immunoassay" as used herein encompasses analytical methods for detecting, locating or quantifying biological substances by use of a label. Generally a label, such as radioactive isotope, is attached to a molecule of the substance of interest. The presence of the labeled molecule can then be detected by suitable means.

There are various types of immunoassay in common use. In one type of immunoassay, a sample, e.g., a solution, containing both an unknown and a labeled antigen of interest is incubated with an antibody specific for that antigen. If the unknown also contains the antigen, then both the labeled and unlabeled antigens compete for binding sites on the antibody. The antibody can be immobilized on a solid support, such as a test tube, glass beads, latex particles, etc. Incubation is followed by a separation step in which the antigen bound to the antibody on the support is separated from unbound antigen. Through measurement of the amount of bound labeled antigen, the presence and/or quantity of similar, unlabeled antigen can be determined. That is, the higher the concentration of antigen in the unknown, the fewer the binding sites occupied by a labeled antigen. Thus, the detected level of the labeled antigen (e.g., counts per minute of radioactivity) is an inverse function of the concentration of the unlabeled antigen.

A second type of immunoassay is known as sandwich immunoassay. In this method, an antibody rather than an antigen is labeled. A sample containing an unknown is incubated with an immobilized antibody. Antigens, if present in the sample, will bind to the antibody. After incubation, unbound material is removed by a separation step. In a second incubation with a solution of labeled antibody, the bound antigen is "sandwiched" between the immobilized antibody and the labeled antibody which adheres to the antigen. After a second separation, the amount of labeled antibody is determined. Detection of labeled antibody is indicative of the presence of antigen.

In general, the most commonly used type of label is a radioactive substance, such as $^{125}I$, which can easily and accurately be detected. However, materials labeled radioactively often have a short shelf life, both because of radioactive decay of the label and because radiation degrades the labeled molecule. Further, handling of radioactive substances entails risks to laboratory personnel.

The present invention is directed to novel compounds which are useful as labels in luminometric immunoassay (hereinafter referred to as "LIA") in both conventional and sandwich assay techniques. Unlike radioimmunoassay, LIA does not employ radioactive materials. Rather, the label attached to the antigen or antibody is a chemiluminescent compound, that is, a compound which can undergo a reaction (usually oxidative) in which light is a product. The light emission is measured by appropriate devices, and in certain cases, the light intensity is indicative of the quantity of labeled material.

Known chemiluminescent substances suitable for use in immunoassays include luminol (5-amino-2, 3-dihydrophthalazine-1, 4-dione), isoluminol (6-amino-2, 3-dihydrophthalazine-1, 4-dione) and the various acridinium esters.

SUMMARY OF THE INVENTION

The present invention is concerned with novel phenanthridinium compounds and their utilization in luminometric immunoassay. Specifically, the compounds of the invention are salts of phenyl-10-methylphenanthridinium9-carboxylate derivatives having the formula:

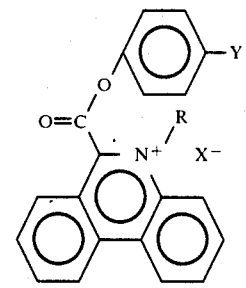

where R is an alkyl group having from 1 to 5 carbon atoms, X is an anion selected from the group consisting of sulfates, alkylsulfates, halosulfonates and halides, and Y is a chemical moiety which may bind to an amino group, carboxyl group, or other groups commonly found in analytes or proteins of interest.

In another aspect of the invention, immunoassays are performed using conjugates of the above compounds and antibodies or antigens. In one embodiment, the immunoassay includes the steps of incubating an immobilized antibody specific to the antigen with a sample solution; incubating the immobilized antibody and bound antigen, if present, with a solution of labeled antibody, to form an immobilized sandwich, said labeled antibody comprising a conjugate of an antibody and a chemiluminescent compound of the formula:

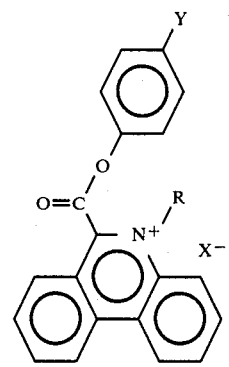

where R is an alkyl group having from 1 to 5 carbon atoms, X is an anion selected from the group consisting of sulfates, alkylsulfates, halosulfonates and halides, and Y is a chemical moiety which may bind to an amino group, carboxyl group, or other groups commonly found in analytes or proteins of interest; separating the solution of labeled antibody from the immobilized sandwich; reacting the labeled antibody in the immobilized sandwich with an oxidizing agent to cause light emission; and measuring the amount of light emitted to determine the presence of antigen.

An alternative immunoassay procedure includes incubating an immobilized antibody with a sample solution and a labeled antigen, said labeled antigen comprising a conjugate of the antigen and a chemiluminescent compound having the formula:

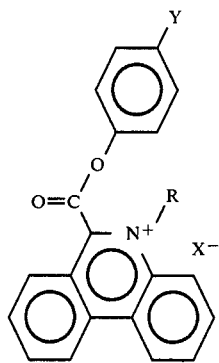

where R is an alkyl group having from 1 to 5 carbon atoms, X is an anion selected from the group consisting of sulfates, alkylsulfates, halosulfonates and halides, and Y is a chemical moiety which may bind to an amino group, carboxyl group, or other groups commonly found in analytes or proteins of interest; separating bound antigen from unbound antigen; reacting the bound labeled antigen with an oxidizing agent to cause light emission; and measuring the amount of light emitted to determine the presence of unlabeled antigen.

As used herein the term "antigen" includes any substance which one wishes to detect in a sample, provided an antibody specific to the substance can be raised. Thus, the term, as used herein, includes substances which may not be immunogenic themselves, but which can be rendered immunogenic by conjugation with an immunogenic carrier molecule in order to elicit the formation of antibodies specific to the substance. For example, steroid hormones naturally present in the body, while not immunogenic themselves, would be considered antigens for purposes of this description, since techniques are available to elicit antibodies specific to steroid hormones.

BEST MODE FOR CARRYING OUT THE INVENTION

Figure 1:
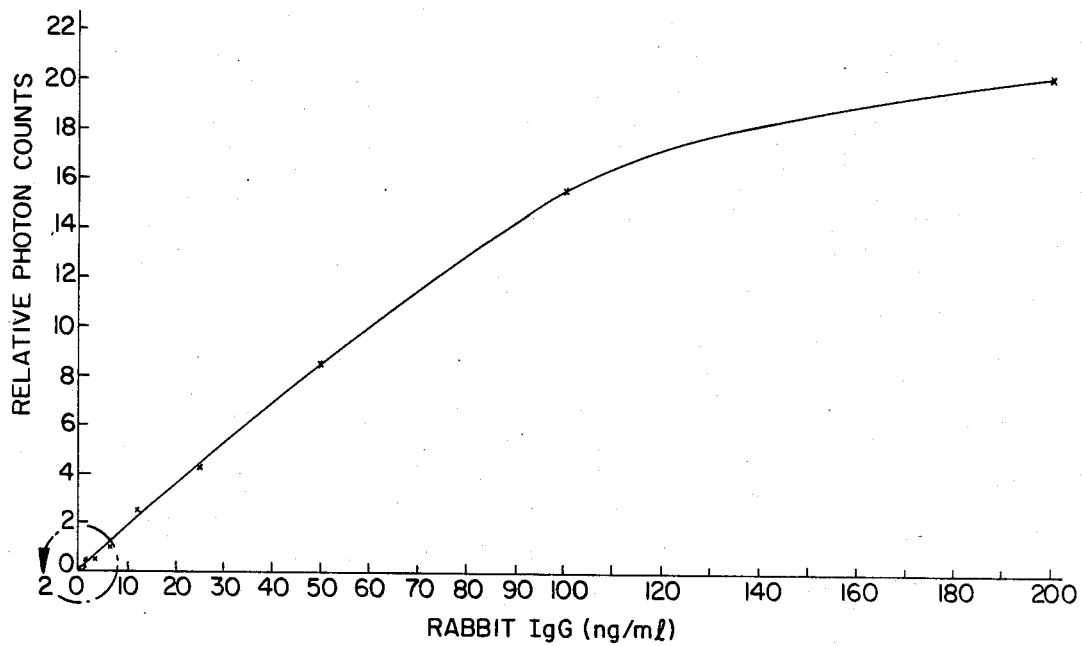
FIG. 1 depicts a rabbit IgG LIA standard curve using a compound of the invention as the chemiluminescent compound.

The chemiluminescent compounds of the invention have the following formula:

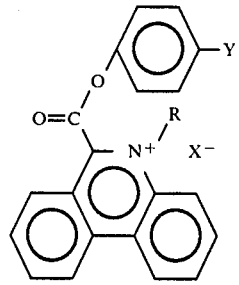

where R is an alkyl group having from 1 to 5 carbon atoms, X is an anion selected from the group consisting of sulfates, alkylsulfates, halosulfonates and halides, and Y is a chemical moiety which may bind to an amino group, carboxyl group, or other groups commonly found in analytes or proteins of interest. Y may be for example an amine, aldehyde, carboxylic acid, N-maleimide, or an N-succinimidyl group. Preferably, Y is a succinimidyloxycarbonyl or a succinimidyloxycarbonylalkyl wherein the alkyl group has from 1 to 5 carbon atoms. Desirably, X is a halosulfonate and, preferably, fluorosulfonate.

The chemiluminescent compounds of the invention can be synthesized from phenanthridine using a series of reactions forming intermediate compounds. The reaction scheme is outlined below, where Y and X are the preferred compounds:

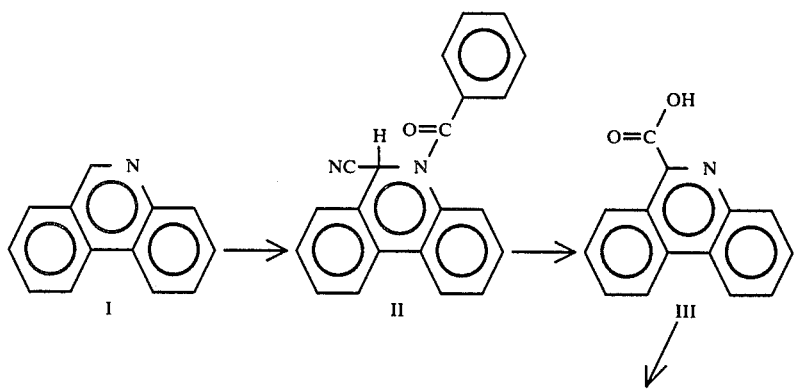

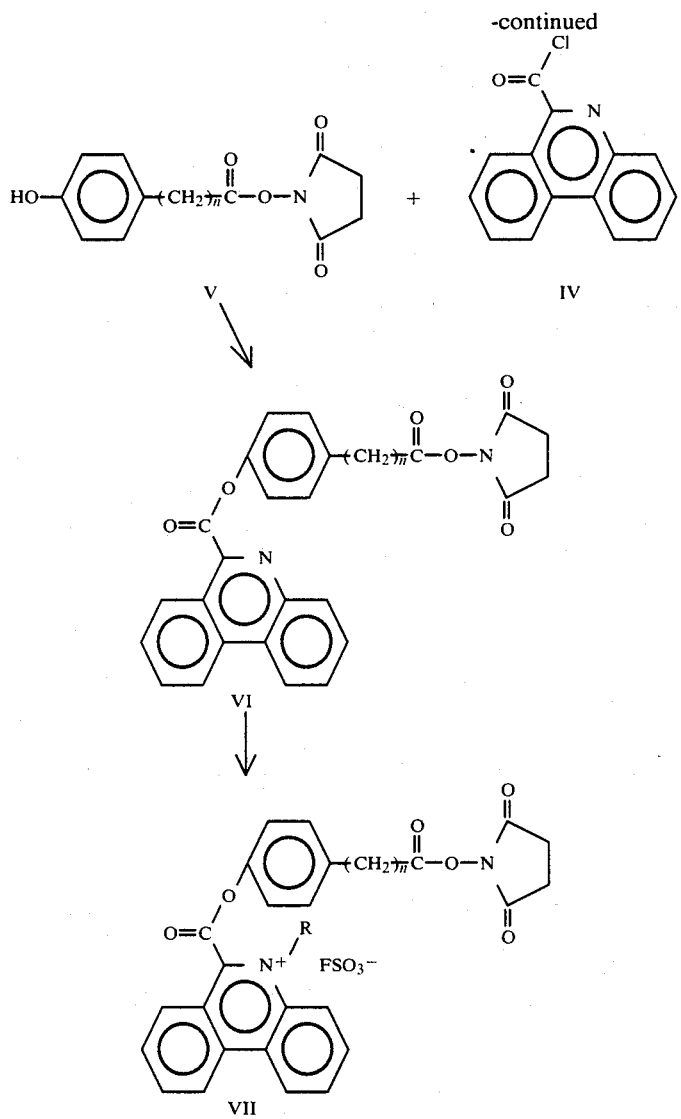

In general, phenanthridine (I) is reacted with hydrocyanic acid and benzoyl chloride to produce a cyanobenzoylhydrophenanthridine compound of formula (II). The compound of formula (II) is reacted with sulfuric acid and sodium nitrite to produce the phenanthridine carboxylic acid compound of formula (III). The acid is converted to the corresponding acid chloride, i.e., a compound of formula (IV), and reacted with a succinimidyloxycarbonylalkylphenol (V), to produce a phenanthridine ester compound of formula (VI). This is followed by conversion to a salt through reaction with ar alkyl halosulfonate compound, producing the phenanthridinium ester salt of formula (VII), i.e., the compound of the invention.

The chemiluminescent compounds of the invention are conjugated to antibodies or antigens through the N-succinimidyl or other group for use in immunoassays. The antibodies can be conventional antisera-type antibodies or, if desired, they can be monoclonal antibodies. Methods for producing antibodies useful in conjunction with the chemiluminescent compounds of the invention are well known to those skilled in the art. Conjugates of the chemiluminescent compounds with antibodies or antigens are prepared by mixing chemiluminescent compounds of the invention with antibodies or antigens in buffer for several minutes at room temperature (usually about 15 minutes). Under these conditions, a peptide bond is formed between the phenanthridinium ester and the antibody or antigen.

In a preferred embodiment of the invention, antibodies labeled with the chemiluminescent compound are employed in a sandwich type immunoassay. In carrying out immunoassays using the labeled antibody or artigen, antibody specific to the antigen of interest is generally immobilized on a solid support such as a test tube wall, glass beads, polystyrene beads, sepharose, latex, or any inert solid matrix. Antibodies can be simply adsorbed on the solid support surface or covalently bound to the matrix.

In the sandwich type immunoassay of the invention, the sample to be tested is placed in a test tube or well containing antibodies immobilized on a solid support. For example, the antibodies may be immobilized on the inner walls of the test tube or test well or the vessel may contain polystyrene or glass beads having the antibody immobilized on the bead surfaces. The sample, generally in the form of a buffered solution, is incubated with the immobilized antibody for a sufficient amount of time to allow the antigen, if present in the sample, to bind to the immobilized antibody. While incubation time may vary somewhat depending upon the particular antigen, the dilution of the sample, temperature, etc., an incubation time of about one hour is generally sufficient to allow binding to occur. The incubation can be carried out at temperatures from about 0° C. to 45° C. and preferably at about ambient temperature.

The sample is then separated from the immobilized antibody and bound antigen by any convenient means, e.g., by aspiration from the test tube or well. After the test tube is washed with a suitable solution, a buffered solution containing the antibody labeled with the chemiluminescent compound of the invention is placed in the test tube or well and incubated for a sufficent period of time to allow binding of labeled antibody to any antigen which might be present. Incubation times and temperatures are generally about the same as those indicated above for the initial incubation. The solution containing the labeled antibody is then separated from the sandwich, comprising labeled antibody, antigen and unlabeled antibody bound to the solid support.

The labeled sandwich on the solid support is then subjected to mild oxidizing conditions in order to generate the emission of light. Oxidizing conditions can be conveniently achieved by adding to the test tube or well a buffered solution of an oxidizing agent such as hydrogen peroxide. The amount of light emitted is measured with any suitable light measuring instrument such as a commercially available luminometer. By comparison of the amount of light emitted from the sample with a standard curve which has been generated for serial dilutions of antigen of known concentration, the amount of antigen present in the sample can be determined.

If desired, a simplified immunoassay procedure can be used in which the first separation step, following incubation of the sample with the immobilized antibody, can be eliminated. For example, a buffered solution of the sample to be tested can be added to a polystyrene test tube having antibodies bound to the inner surface of the test tube walls. Subsequently, a buffered solution of labeled antibody is added to the test tube without removal of the sample solution and the mixture is incubated.

In this procedure the antigen containing two or more antibody binding sites will bind separately with two different types of antibodies. Since two different types of antibodies do not compete at the same binding site, this method provides a simple and quick test procedure without sacrificing the sensitivity of the assay. This procedure is typically used when one wishes to determine the presence of a polypeptide in a sample, e.g., an immunoassay for the presence of herpes viral antigen. While immunoassay procedures have been described in detail with respect to the preferred sandwich type immunoassay, the chemiluminescent compounds of the invention can also be used with other types of immunoassay procedures, such as the procedure previously described in which labeled antigen competes with unlabeled antigen in a sample for binding to antibodies immobilized on a solid support.

The immunoassay procedures described herein can be employed to detect and quantitate any antigen for which specific antibodies can be raised. One can mention, as merely illustrative of the types of antigens one may wish to detect, virus antigens such as herpes, hepatitis, influenza and the like, polypeptides such as thymosin alpha$_1$, interleukins, endorphins, enkaphalins, human chorionic gonadotropin, alpha-fetoprotein and the like, steroid hormones, various drug substances, and analytes of interest.

The examples which follow illustrate the synthesis of phenanthridinium ester salts of the invention and their utilization in immunoassays.

Examples 1 through 4 describe the synthesis of intermediates and two compounds of the invention.

Figure 2:
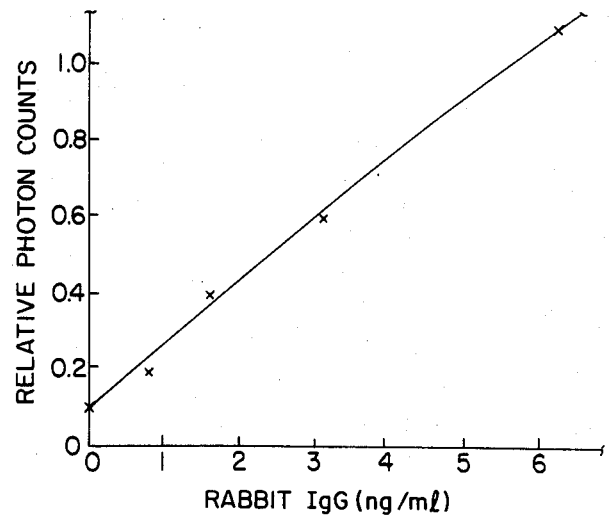
FIG. 2 is a portion of the curve of FIG. 1 expanded for clarity.

Example 5 describes the preparation of antibody conjugates in which purified donkey antibody against rabbit IgG and IgG fraction of hyperimmunized rabbit serum were (separately) combined with phenanthridinium ester salts. Example 6 illustrates how a standard curve can be produced for detecting antigens. The results are summarized in Table I, FIG. 1 and FIG. 2. The standard curve can then be used for quantitative measurement of an unknown such as herpes antigen, as in example 7. Table II summarizes the results of a herpes sandwich LIA. In addition to the formulas already given, the following compounds will at times be referred to in the examples by numeral only:

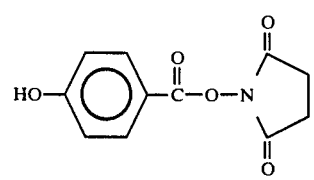

VIII

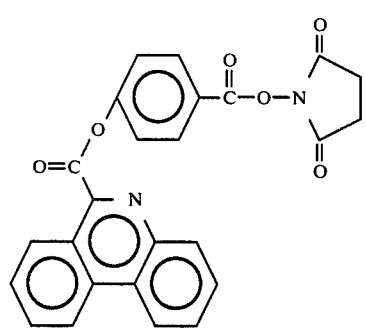

IX

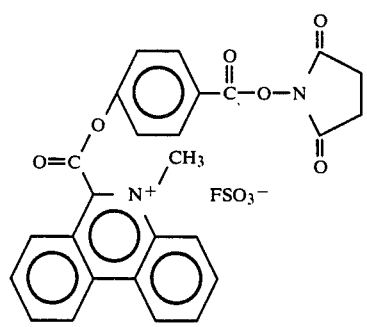

X

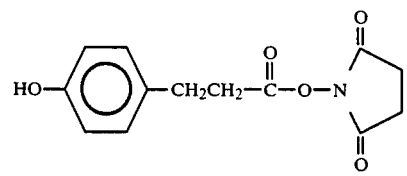

XI

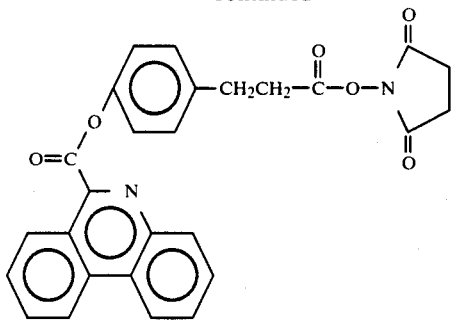

XII

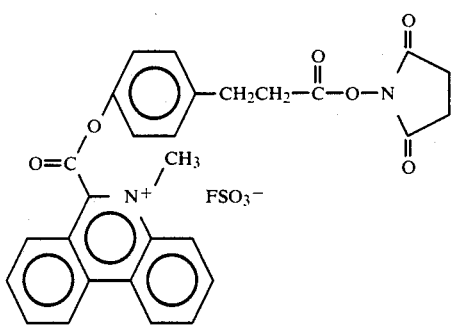

XIII

EXAMPLE 1

Preparation of 9-Cyano-10-benzoyl-9-hydrophenanthridine (II)

A slurry of 10.0 gm (55.8 m mol) phenanthridine (I) and about 12 ml of anhydrous hydrocyanic acid in 20 ml of dry toluene was prepared. This slurry was cooled in an ice water bath, and a solution of 4.0 gm (28.5 m mol) benzoyl chloride in 20 ml of dry toluene was added dropwise to it. In doing so, the phenanthridine solubilized upon stirring. The mixture was stirred at ice water temperature for 4 hours and then at room temperature overnight. A small amount of precipitate had formed after the first hour of stirring. The precipitation was increased by the addition of 75 ml diethyl ether. Upon extraction with deionized water and dilute sulfuric acid, the precipitate was redissolved. The organic solution was washed twice with deionized water. Phenanthridine (4.9 gm) was recovered by adding concentrated ammonium hydroxide solution to the aqueous layer. After washing the organic layer with a saturated sodium bicarbonate solution and then with water, the diethyl ether and toluene were completely removed under reduced pressure. Crystallization from ethyl alcohol (95%) gave an 8.3 gm (95.9%) yield of compound II, mp 140.5°–141.5° C.

EXAMPLE 2

Preparation of Phenanthridine-9-carboxylic Acid (III)

Compound III was synthesized by a modification of the procedure of British Patent No. 1,461,877 to McCapra, et al., for the preparation of acridine-9-carboxylic acid. In a 200 ml flask was placed a mixture of 2.0 gm (6.5 m mol) of compound II in 10 ml of concentrated sulfuric acid. The mixture was stirred at 100°–110° C. for 3 hours and then cooled in an ice water bath. To the stirred, viscous solution was added portionwise, powdered sodium nitrite (4.0 gm). The flask was then carefully heated on a hot plate. Since vigorous evolution of nitrogen oxides occurred, it was sometimes necessary to remove the flask from the hot plate in order to slow down the reaction.

The hot, viscous mixture was slowly poured into a stirred ice and water mixture. The yellow precipitate was collected by suction filtration, washed with water, and drained thoroughly. The product was dissolved in an ice cooled sodium hydroxide (2N) solution. The undissolved substances were removed by filtration. After acidification with concentrated hydrochloric acid at ice water temperature, the yellow solution was stored in a refrigerator overnight. The resulting precipitate was filtered, washed with water, and dried in a vacuum oven at 35°–40° C., yielding 0.43 gm of compound III, mp 155° C. with decomposition (lit. 155° C.). The general procedure is summarized in an article by Von Georg Wittig, Margeris A. Jesaitis, and Martin Glos, *Ann. der. Chemie*, 577, 1 (1952).

EXAMPLE 3

Synthesis of 4-(N-succinimidyloxycarbonyl) pnenyl-10-metnylphenanthridinium-9-carboxylate fluorosulfonate (X)

To a 100 ml round bottom flask equipped with a condenser was added 7.2 gm (32.3 m mol.) of compound III and 15 ml of thionyl chloride. A drying tube attached to the top of the condenser was used to protect the system from moisture. The mixture was refluxed for 10 min. with stirring. The excess thionyl chloride was removed by rotary evaporation. In order to remove remaining thionyl chloride, dry toluene (40 ml) was added to the product and was then evaporated under reduced pressure. The acid chloride of compound IV thus formed was used without further purification. Dry toluene (30 ml) was added to the flask containing the acid chloride. To this slurry was added dropwise a solution of 9.0 gm (38.3 m mol.) of N-succinimidyl-4-hydroxybenzoate of compound VIII in 25 ml of dry toluene and 10 ml of anhydrous triethyl amine. The mixture was stirred at room temperature for 4 hours. The triethyl amine hydrochloride formed was removed by filtration. The solvent was removed from the filtrate at reduced pressure. The brown solid of compound IX obtained was used without further purification.

Compound IX was dissolved in 200 ml of dry methylene chloride. Methyl fluorosulfonate (20 ml) was added and the mixture was stirred at room temperature overnight. The yellow precipitate (compound X) was collected by suction filtration and washed with methylene chloride. Compound X was recrystallized by dissolution in acetonitrile (100 ml) with subsequent precipitation by diethyl ether (700 ml). A further recrystallization from 95% ethanol gave a pure product, mp. 258°–259° C.

EXAMPLE 4

Preparation of 4-(2-N-Succinimidyloxycarbonylethyl) phenyl-10-methylphenanthridinium-9-carboxylate Fluorosulfonate (XIII)

To a solution of crude phenanthridine-9-carboxyl chloride of compound IV obtained from 7.2 gm (32.3 m mol) of phenanthridine-9-carboxylic acid of compound III in 30 ml of dry toluene, was added, dropwise, 12.0 gm (46 m mol) of 4-(2-N-succinimidyloxycarbonylethyl) phenol of compound XI in 25 ml of anhydrous toluene and 10 ml of anhydrous triethyl amine. The mixture was stirred at room temperature for 4 hours. The precipitate was removed by suction filtration. The filtrate was evaporated to give compound XII. This ester, XII, was used without further purification.

Compound XII was dissolved in 200 ml of dry methylene chloride, and 20 ml of methyl fluorosulfonate was added to the mixture. The mixture was stirred overnight at room temperature, and then the yellow precipitate formed was collected by filtration. The solid was recrystallized by dissolution in 100 ml of acetonitrile with subsequent precipitation by 700 ml of ethyl ether to give 6.8 gm (26% yield) of well defined pale yellow crystals of compound XIII, mp 202°–206° C.

EXAMPLE 5

Preparation of Phenanthridinium Ester-Antibody Conjugates

For rabbit IgG LIA, about 1.0 mg of affinity purified donkey antibody against rabbit IgG and 0.5 mg of 4-(2-N-succinimidyloxycarbonylethyl) phenyl-10-methyl phenanthridinium-9-carboxylate of compound XIII were used. In herpes LIA, 2.25 mg of IgG fraction of hyperimmunized rabbit serum and 0.75 mg of 4-(N-succinimidyloxycarbonyl) phenyl-10-methylphenanthridinium-9-carboxylate of compound X were used in the conjugation.

N,N-dimethyl formamide (DMF) (35 ul) containing the proper amount of phenanthridinium ester was added to the corresponding amount of antibody in 0.5 ml pH 8.5 phosphate buffer (0.02M). The mixture was stirred at room temperature for 15 minutes. The mixture was cooled in an ice-water bath for 2 minutes before adding 500 ul of 0.1M citrate buffer pH 4.5 (quenching solution). The reaction mixture was transferred to a 1.0 cm×50 cm Sephadex G-25-150 (Pharmacia) column equilibrated with 0.05M citrate buffer pH 5.0 with 1.0% sodium chloride and 0.01% thimerosal. The protein fractions were collected and the luminosity was quantitated.

EXAMPLE 6

One Step Sandwich Luminometric Immunoassay (LIA) ror Rabbit IgG

The assay was set up in triplicate in 12×75 cm polystyrene tubes which had been preadsorbed with goat antibodies against rabbit IgG. The buffer used throughout this LIA was 0.02M phosphate, pH 6.3 containing 0.15M sodium chloride, 0.1% BSA, and 0.01% thimerosal.

Rabbit IgG antigen standard (100 ul), ranging from 0.8 ng/ml to 200 ng/ml, was added to the antibody-coated tubes. Subsequently 100 ul of chemiluminescently labeled antibody was added. The mixture was gently vortexed and then incubated at room temperature for 3 hours. At the end of the incubation period, 1.0 ml of buffer was added to each tube and was subsequently decanted. The tubes were then washed twice with 1.0 ml of buffer. The last washing solution was left in the tubes until just prior to the light measurement. For the measurement of chemiluminescence, the final washing solution was decanted and the tube was injected with 200 ul of 0.5M borate buffer, pH 12.5, containing 2 ul of a 3% hydrogen peroxide solution. The light emitted was measured with a Turner Designs Luminometer Model 20 and expressed as relative photon counts integrated over 5 seconds. The results and the standard curve for rabbit IgG LIA are given in Table I and FIG. 1 and FIG. 2.

EXAMPLE 7

Sandwich LIA for Herpes

Polystyrene beads, 5/16" in diameter, with a specular finish were pretreated with rabbit antibodies against herpes in 0.1M carbonate buffer, pH 9.6. In the assay the beads were shaken with 300 ul of various dilutions of herpes infected media in 0.02M phosphate buffer, pH 7.4 containing 0.1% BSA and 0.1% sodium azide for 2 hours at room temperature. At the end of the incubation, 2 ml of 0.02M phosphate buffer, pH 7.4, was added to each tube, and the liquid was removed by aspiration. The beads were then washed twice with 2 ml of phosphate buffer. Subsequently the beads were shaken with 300 ul of antibody-compound X conjugate in 0.02M phosphate buffer, pH 7.4, containing 0.1% sodium azide and 25% fetal calf serum for 2 hours at room temperature. After three washes, following the same washing procedure as mentioned above, the beads were transferred to new tubes. Two hundred ul of 0.01M citrate buffer, pH 4.0, was added to each tube, and the tube was placed in a Turner Designs Luminometer Model 20. The chemiluminescence reaction was initiated by the rapid injection of 200 ul of 0.5M borate buffer, pH 10.5, containing 2 ul of a 3% hydrogen peroxide solution. The relationship between herpes virus dilution and relative light production is shown in Table II.

TABLE I

| Rabbit IgG LIA Standard Curve | |
|---|---|
| Rabbit IgG Concentration ng/ml | Relative Photon Counts |
| 0 | 0.1 |
| 0.8 | 0.2 |
| 1.6 | 0.4 |
| 3.1 | 0.6 |
| 6.2 | 1.1 |
| 12.5 | 2.5 |
| 25.0 | 4.3 |
| 50.0 | 8.5 |
| 100.0 | 15.6 |
| 200.0 | 20.3 |

TABLE II

| Herpes Virus Dilution and Relative Photon Counts in Herpes LIA | |
|---|---|
| Virus Dilution | Relative Photon Counts |
| 0 Virus | 0.73 |
| 1:3200 dilution | 1.44 |
| 1:1600 dilution | 2.37 |
| 1:800 dilution | 3.04 |
| 1:100 dilution | 12.97 |

The above description and examples illustrate the best mode and the preferred embodiments of the invention, as required by the Patent Statutes. The invention, however, is not to be construed as being limited thereby or thereto, but rather is intended to encompass modification and changes which will occur to those skilled in the art.

I claim:

1. A chemiluminescent compound of the formula:

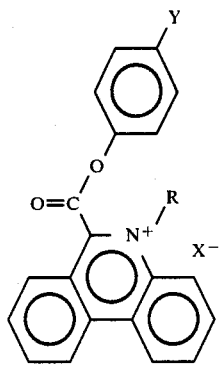

where R is an alkyl group having from 1 to 5 carbon atoms, X is an anion selected from the group consisting of sulfates, alkylsulfates, halosulfonates and halides, and Y is a chemical moiety which may bind to groups commonly found in analytes.

2. A chemiluminescent compound as in claim 1, wherein the compound is:

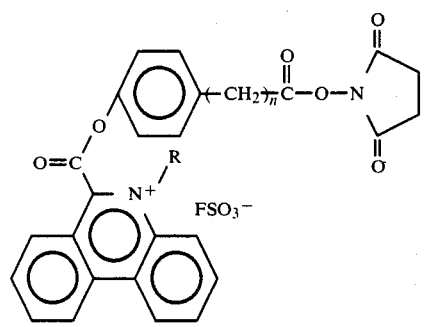

where n is an integer from 0 to 5.

3. A chemiluminescent compound as in claim 2, wherein the compound is:

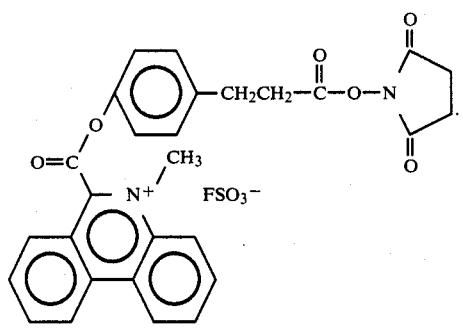

4. A chemiluminescent compound as in claim 2, wherein the compound is:

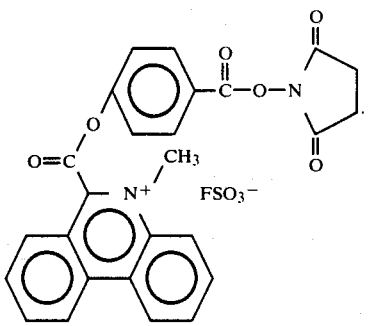

5. A chemiluminescent reagent useful in a luminometric immunoassay, comprising a conjugate of the compound of claim 1 with an antibody.

6. A chemiluminescent reagent useful in a luminometric immunoassay, comprising a conjugate of the compound of claim 1 with an antigen.

7. A luminometric immunoassay for detection of an antigen in a sample, comprising:
  incubating an immobilized antibody specific to the antigen with a sample solution and a solution of labeled antibody; and
  forming thereby an immobilized sandwich, said labeled antibody comprising a conjugate of an antibody and a chemiluminescent compound of the formula:

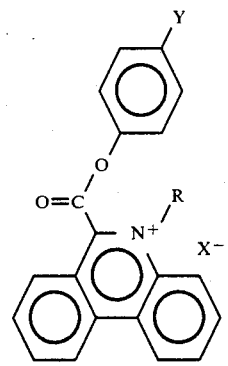

where R is an alkyl group having from 1 to 5 carbon atoms, X is an anion selected from the group consisting of sulfates, alkylsulfates, halosulfonates and halides, and Y is a chemical moiety which may bind to groups commonly found in analytes;
  separating the solution of labeled antibody from the immobilized sandwich;
  reacting the labeled antibody in the immobilized sandwich with an oxidizing agent to cause light emission; and
  measuring the amount of light emitted to determine the presence of antigen.

8. A luminometric immunoassay as in claim 7, wherein, prior to addition of the solution of labeled antibody, the sample solution is separated from the immobilized antibody.

9. A luminometric immunoassay for detection of an antigen in a sample, comprising:
  incubating an immobilized antibody with a sample solution and a labeled antigen, said labeled antigen comprising a conjugate of the antigen and a chemiluminescent compound having the formula:

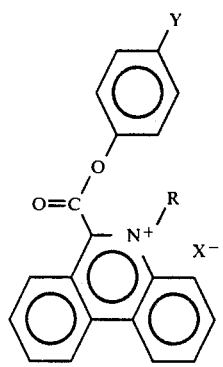

where R is an alkyl group having from 1 to 5 carbon atoms, X is an anion selected from the group consisting of sulfates, alkylsulfates, halosulfonates and halides, and Y is a chemical moiety which may bind to groups commonly found in analytes;

separating bound antigen from unbound antigen;

reacting the bound labeled antigen with an oxidizing agent to cause light emission; and measuring the amount of light emitted to determine the presence of unlabeled antigen.

10. A luminometric immunoassay as in claim 7 or 8, wherein the chemiluminescent compound is:

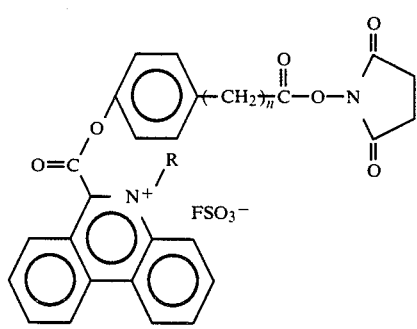

where n is an integer from 0 to 5.

11. A luminometric immunoassay as in claim 10, wherein the chemiluminescent compound is:

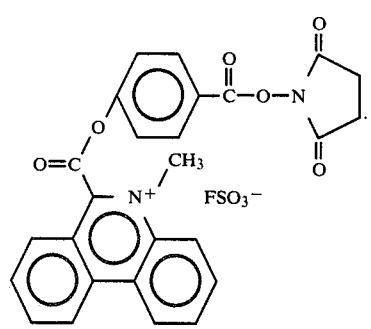

12. A luminometric immunoassay as in claim 10, wherein the chemiluminescent compound is

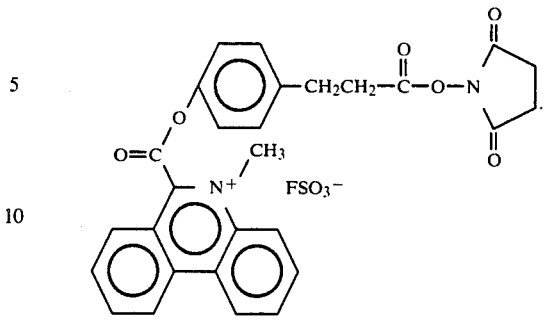

13. A luminometric immunoassay as in claim 9, wherein the chemiluminescent compound is

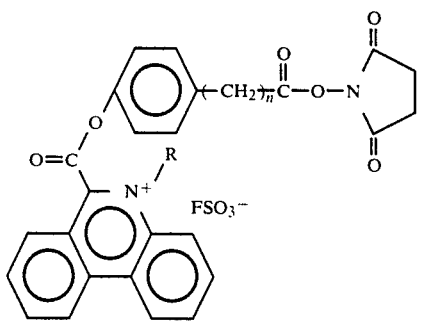

where n is an integer from 0 to 5.

14. A luminometric immunoassay as in claim 13 wherein the chemiluminescent compound is

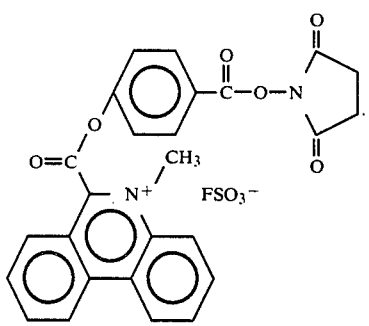

15. A luminometric immunoassay as in claim 13, wherein the chemiluminescent compound is

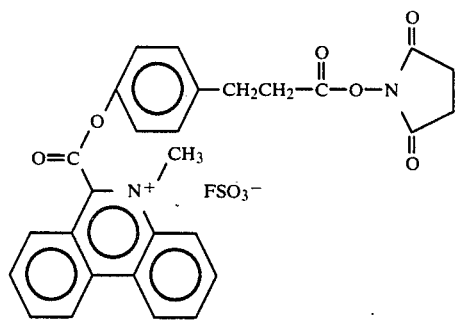

* * * * *